United States Patent [19]

Costerton et al.

[11] Patent Number: 5,312,813
[45] Date of Patent: May 17, 1994

[54] BIOFILM REDUCTION METHOD

[75] Inventors: John W. F. Costerton, Calgary; Antoine E. Khoury, Willowdale; Frank Johnson, Ottawa, all of Canada

[73] Assignee: University Technologies International, Canada

[21] Appl. No.: 918,740

[22] Filed: Jul. 22, 1992

Related U.S. Application Data

[63] Continuation-in-part of Ser. No. 694,980, May 3, 1991, abandoned.

[51] Int. Cl.$^5$ .................. A01N 43/04; A01N 37/18; A01N 43; A01N 42; A61K 31/43; A61K 31/47; A61K 31/545; A61K 31/65; A61K 31/70

[52] U.S. Cl. ........................... 514/29; 514/31; 514/34; 514/37; 514/39; 514/41; 514/152; 514/153; 514/154; 514/198; 514/199; 514/200; 514/201; 514/202; 514/203; 514/204; 514/205; 514/206; 514/207; 514/208; 514/209; 514/312; 514/460; 606/32; 606/33; 606/34; 43/98; 607/122; 607/126; 607/134; 607/138

[58] Field of Search ............... 514/25, 29, 31, 34, 514/37, 39, 41, 152, 153, 154, 198, 199, 200, 201, 202, 203, 204, 205, 206, 207, 208, 209, 312, 460; 606/32, 33, 34; 128/82.1, 362, 419 N, 783, 784, 785, 786, 787, 788, 419 R, 419 S; 43/98

[56] References Cited

PUBLICATIONS

Khoury et al., "Prevention and Control of Bacterial Infections Associated with Medical Devices" ASAIO Transactions, Jul./Sep. 1992, vol. 38, No. 3, pp. M 174–178.

*Primary Examiner*—Nathan M. Nutter
*Attorney, Agent, or Firm*—Carol A. Stratford; Peter J. Dehlinger

[57] ABSTRACT

A method of killing microorganisms which form a biofilm on a tissue or implant surfaces in a patient, and which are refractory to a biocide at a dose which is effective to kill the microorganism in planktonic form. The effect of the biocide is potentiated, to an effective killing level, by applying an electric field across the surface containing the biofilm.

9 Claims, 7 Drawing Sheets

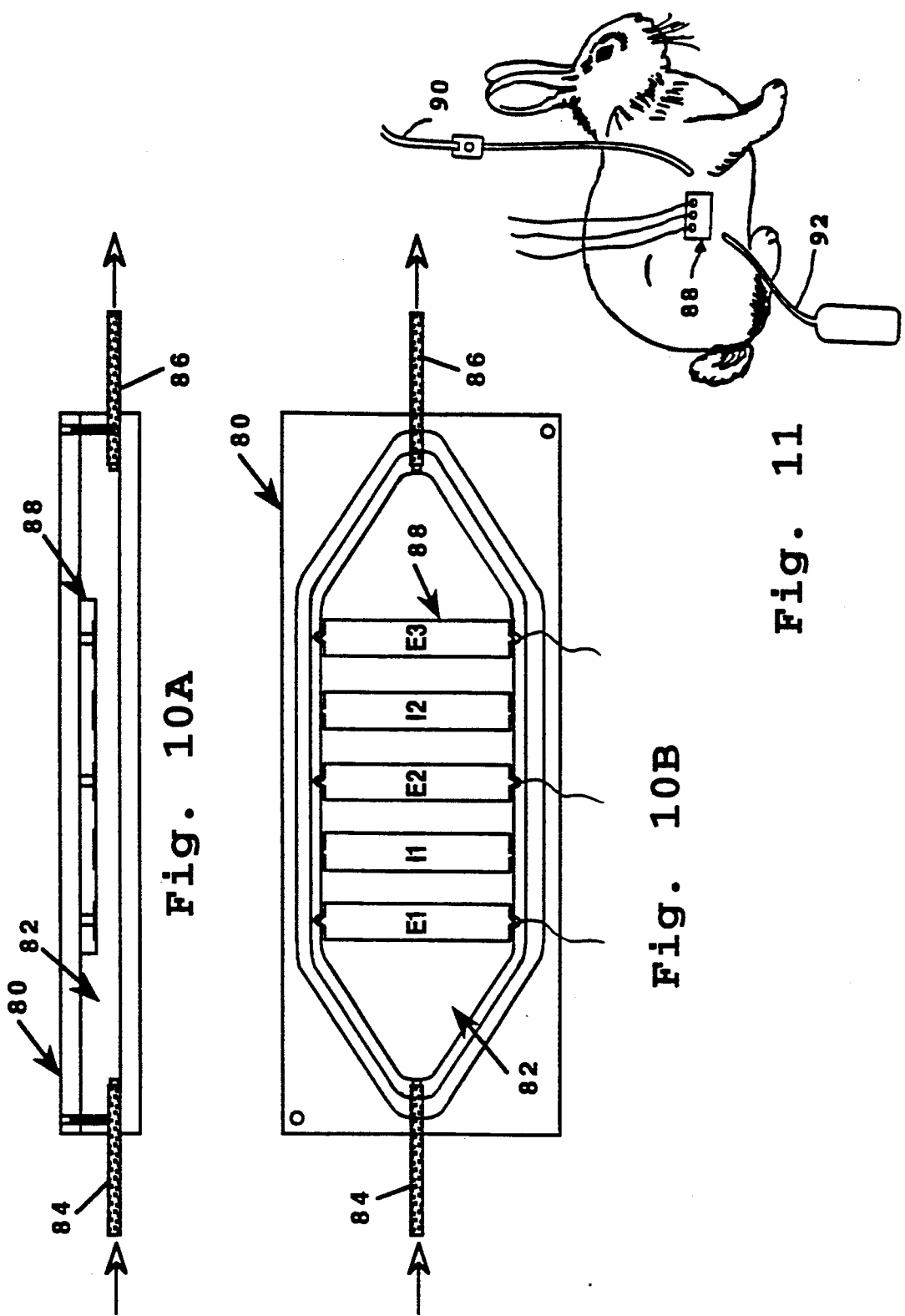

BIOFILM REDUCTION METHOD

This is a continuation-in-part application of application Ser. No. 07/694,980, filed May 3, 1991 and now abandoned.

FIELD OF THE INVENTION

The present invention relates to a method of biofilm reduction.

REFERENCES

Costerton, J. W., et al., Ann. Rev. Microbiol. 41:435–464 (1987).

Costeron, J. W., Irvin, R. T., Cheng, K.-J., Ann. Rev. Microbiol. 35:299–324 (1981).

Gristina, A. G. and Costerton, J. W., Ortho.Clin. of N.America 15:517–535 (1984).

Jacques, M., Marrie, T. J., Costerton, J. W., Microb. Ecol. 13:173–191 (1987).

LeChevallier, M. W. et al., Appl. Environ. Microbiol. 54:2492–2499 (1988).

Nickel, J. C., et al., Antimicrob. Agents Chemother. 27:619–624 (1985a).

Nickel, J. C., Wright, J. B., Ruseska, I., Marrie, T. J., Whitfield, C., and Costerton, J. W., Eur. J. Clin. Microbiol. 4:213:218 (19856).

Passerini, L., Phang, P. T., Jackson, F. L., Lam, K., Costerton, J. W., King, E. G., Chest 92:440–446 (1987).

Read, R. R., Eberwein, P., Dasgupta, M. K., Grant, S. K., Lam, K., Nickel, J. C., and Costerton, J. W., Kidney Int'l 35:614–621 (1989).

Reed, W. P., Moody, M. R., Newman, K. A., Light, P. D., Costerton, J. W., Surgery 99:308–317 (1986).

Warren, J. W., Tenney, J. H., Hoopes, J. M., Muncie, H. L., Anthony, W. C., J. Inf. Duo 146:719–723 (1982).

BACKGROUND OF THE INVENTION

In natural environments, and particularly in aquatic environments, certain microorganisms preferentially exist in sessile, colony-forming cells which form a biofilm. A biofilm is a conglomerate of microbial organisms embedded in a highly hydrated matrix of exopolymers, typically polysaccharides, and other macromolecules (Costerton 1981). Biofilms may contain either single or multiple microbial species and readily adhere to such diverse surfaces as river rocks, soil, pipelines, teeth, mucous membranes, and medical implants (Costerton, 1987). By some estimates biofilm-associated cells outnumber planktonic cells of the same species by a ratio of 1000–10,000:1 in some environments.

Prevention of colonization by and eradication of biofilm-associated microorganisms is an important, and often difficult, problem in medicine. Unlike planktonic organisms, which are relatively susceptible to biocides, e.g, antibiotics, the structural matrix established during biofilm formation can make the colonizing cells able to withstand normal treatment doses of a biocide. It is known that when organisms are isolated from biofilms and then grown in planktonic culture, they lose many of the characteristics associated with the progenitor cells, in particular, the ability to produce a glycocalyx (Costeron, 1987). In the biofilm, the glycocalyx matrix appears to serve as a barrier which protects and isolates the microorganisms from host defense mechanisms such as antibodies and phagocytes as well as from antimicrobial agents including surfactants, biocides and antibiotics (Costerton, 1981). In one study, biofilm-associated bacteria were able to survive a concentration of antibiotic 20 times the concentration effective to eliminate the same species of bacteria grown in planktonic culture (Nickel, 1985a). The higher doses of biocides needed to eliminate biofilm growth may not well tolerated in the body.

Biofilm infections can occur in a variety of disease conditions. In some tissue infections, such as prostatitis, the infective bacterium is capable of growing in the infected tissue in both biofilm (sessile) and circulating (planktonic) form (Costerton, 1987). Although growth of the planktonic cells can be controlled by antibiotic treatment, the biofilm itself may be refractory to treatment, providing, in effect, a reservoir of infection which can lead to recurrence of the infection after antibiotic treatment.

Osteomyelitis is another biofilm-associated bacterial infection which can be difficult to treat. In severe cases, the infected bone must be exposed operatively, and the interior of the bone scraped to remove infected regions. The bone is then packed with a matrix material which serves as a carrier for an antibiotic. Even with this extreme treatment, the biofilm infection may not be completely destroyed, and further such treatment may be necessary (Gristina, 1984).

Biofilm infection is also associated with septic arthritis, where biofilm formation on joint surfaces can lead to a chronic and recurrent infection In addition to sepsis, the biofilm infection can cause destruction of the joint surface material (Gristina).

Biofilm formation can also be a serious complication in bio implants, such as bone prostheses, heart valves, pacemakers and the like. Biofilm formation on exposed surfaces of a bio implant can degrade the function of the implant (Passerini), as in the case of implanted valves, lead to serious joint or bone infections, as in the case of a bone prosthesis (Gristina), and in all cases, provide a source of difficult-to-treat septic infection (Jacques).

SUMMARY OF THE INVENTION

It is one object of the invention to provide an improved method of killing microorganisms in a biofilm.

A more specific object of the invention is to provide a method of potentiating the action of biocides in killing biofilms.

In one aspect, the invention includes a method of killing microorganisms which form a biofilm on a surface expanse. The biofilm is refractory to killing when a biocide is contacted with the biofilm at a planktonic biocidal concentration (PBC) which is effective in killing the microorganism in a planktonic, but not in a biofilm form. In practicing the method, the biofilm is placed in contact with the biocide, at a planktonic biocidal concentration, and an electric field is applied across the film. The strength and duration of the field are such as to produce killing of microorganisms forming the biofilm, in the presence of the biocide.

In a typical embodiment, the biofilm is composed predominantly of bacteria, and the biocide is an antibiotic, such as one of the penicillins, cephalosporins, aminoglycosides, tetracyclines, sulfonamides, and quinolones.

The electric field is preferably applied across a pair of electrodes, at a voltage level sufficient to produce a current density between electrodes of between about 5–25 $\mu A/cm^2$.

For treating infected regions which are in or adjacent vessels, the electric field may be established by first accessing the vessel region by a catheter, and using the catheter as a non-ground electrode.

Also forming part of the invention is a method of potentiating the effect of a biocide in killing microorganisms which form a biofilm on a surface expanse in a liquid environment. The biocide is potentiated by generating across the biofilm, an electric field whose field strength and duration are sufficient to produce killing of the biofilm microorganisms, in the presence of a biocide, where the concentration of the biocide is less than that effective to kill the biofilm microorganisms in the absence of the electric field.

These and other objects and features of the invention will become more fully apparent when the following detailed description of the invention is read in conjunction with the accompanying drawings.

BRIEF DESCRIPTION OF THE DRAWINGS

FIGS. 10A and 10B are side and top views, respectively, of a flow cell and electrode plate used for testing the effect of an electric field on the viability of biofilm cells; and FIG. 11 shows the placement of the electrode plate from FIG. 10 at an intraperitoneal site of a rabbit, for use in testing the effect of electric field on a biofilm in vivo.

DETAILED DESCRIPTION OF THE INVENTION

A. Biofilm Formation and Characteristics

Figure 1:
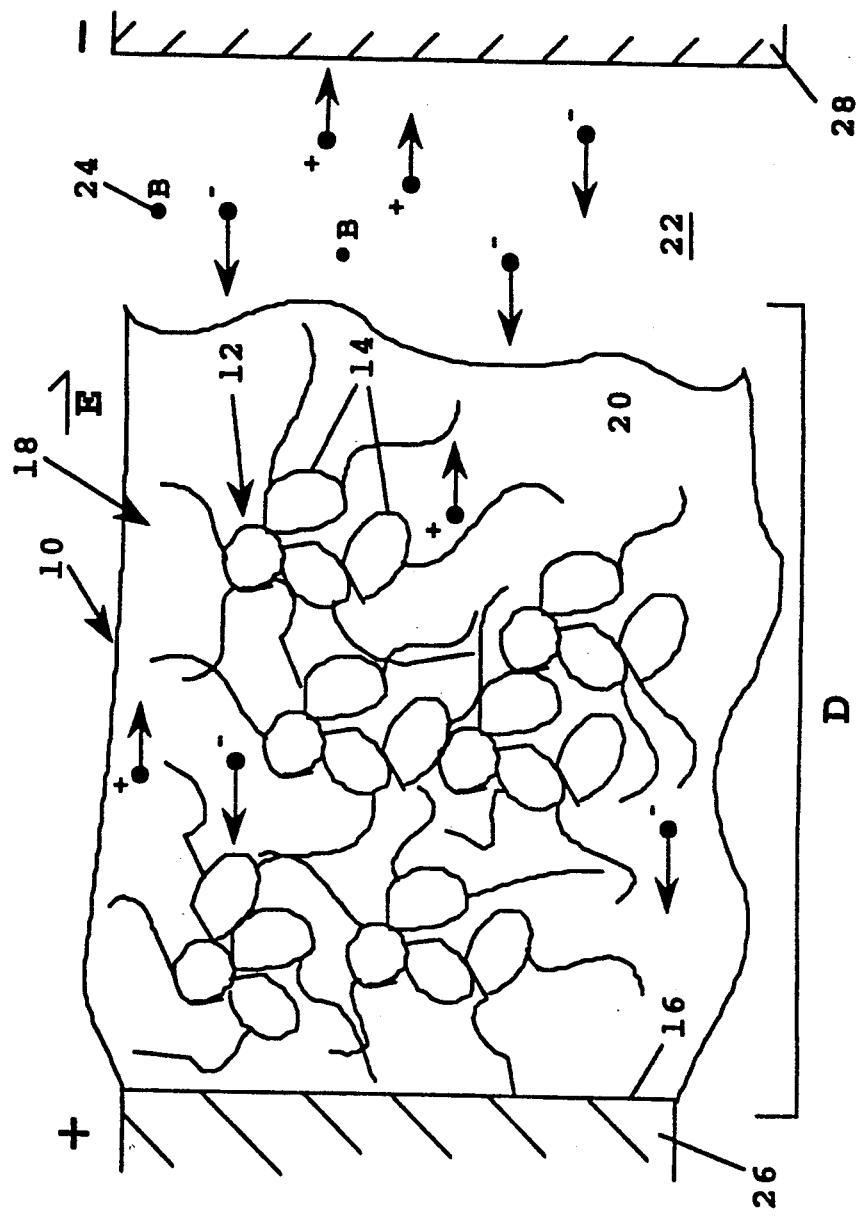
FIG. 1 illustrates a surface expanse and a biofilm growing on the expanse.

Biofilms are composed of colonies of microorganisms, typically bacterial cells, but also colonies of yeast or other colonizing microorganisms. FIG. 1 is a representation of a biofilm 10 formed of clumps or colonies 12 of cells, such as cells 14, which are anchored to a surface expanse 16.

The cells in a biofilm are embedded in a hydrated matrix 18 of exopolymers and other filamentous macromolecules, typically glycopeptides, such as indicated at 20 in FIG. 1. The matrix formed by the filamentous material serves to anchor and coalesce the cells in the biofilm. The matrix, along with other cellular changes which occur on colonization, serves to protect colonized cells against biocidal agents to which the biofilm may be exposed, as discussed below.

The surface expanse and biofilm formed thereon are in contact with an aqueous medium, indicated at 22. The medium may be a defined electrolyte solution or a body fluid, such as blood or lymph, which supplies the tissue on which the biofilm is formed. The medium may carry planktonic cells onto the biofilm, where the cells may become incorporated in the biofilm; conversely, sessile cells in the biofilm may break off, individually or in clumps to form part of a circulating cell population.

In accordance with the present invention, the aqueous medium in contact with the biofilm contains a biocide, such as indicated at 24 by biocide molecules B. As noted above, the microorganisms in the biofilm have a substantially higher tolerance for the biocide than the same microorganisms in free, i.e., planktonic form.

The greater resistance to biocides of microorganisms in a biofilm, when compared with the same cells in planktonic form, has been established for a variety of microorganisms. Among bacteria, this phenomenon has been shown for P. aeruginosa, Klebsiella pneumoniae and E. coli. The concentration of antibiotic needed to kill substantially all cells in biofilm, herein referred to as the biofilm biocidal concentration (BBC), can range from 2 up to 50 times the concentration required for substantially complete killing in planktonic form, also known as the planktonic biocidal concentration (PBC). Similarly, it has been shown that yeast-cell biofilms are resistant to much higher concentrations of antibiotic, such as cycloheximide, than the yeast cells in planktonic form.

Figure 2:
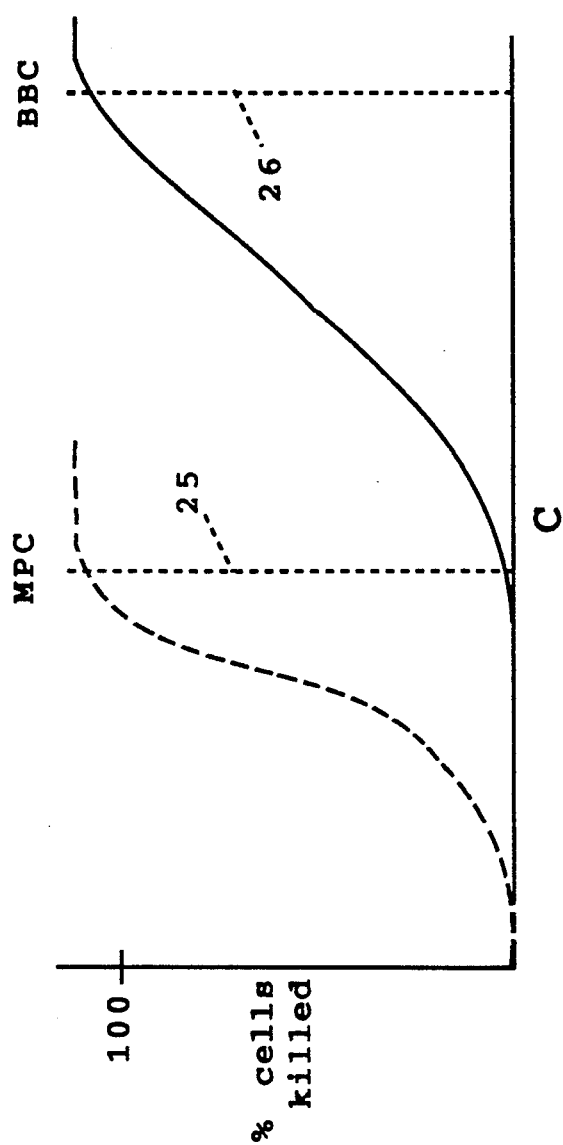
FIG. 2 is a hypothetical concentration-effect curve for biocidal killing of planktonic (dotted line) and biofilm (solid line) microorganisms.

FIG. 2 shows an idealized dose response curve bacterial cell killing at increasing concentration of antibiotic, for cells in planktonic (dotted lines) and biofilm (solid line) form. The line indicated at 24 in the figure is the PBC concentration at which substantially all of the planktonic cells are killed. As seen, only a relatively small percent of biofilm cells are killed at this concentration.

Although more of the biofilm cells will be killed at biocide concentrations above the PBC, increasingly higher drug levels may be impractical or undesirable, particularly at concentrations needed to kill substantially all of the biofilm cells. As will be seen below, and according to an important feature of the present invention, it has been discovered that the biofilm dose-response curve for cell viability can be shifted toward lower drug concentration by subjecting the biofilm cells to an applied electric field. This shift has the effect of producing substantially complete biofilm cell killing at concentrations above the PBC, but below the biofilm biocidal concentration (BBC) needed to produce complete biofilm killing under normal (zero electric field) conditions, indicated by line 26 in the figure.

With reference again to FIG. 1, the biofilm is shown in between electric field E generated by a pair of electrodes 26, 28. The field is produced by a placing a voltage potential across the electrodes, as indicated by "+" and "−" electric polarity symbols on the electrodes. As seen, ions (charges solute species, indicated by "+" and "−" symbols) in the biofilm and surrounding aqueous medium serve as current carriers between the two electrodes, with ion migration occurring in the aqueous medium and through the biofilm in the direction of the arrows in the figure.

According to an important feature of the invention, it has been discovered that a biofilm, such as the one shown in FIG. 1, is substantially more susceptible to cell killing by a biocide when the biofilm is placed in an electric field, as shown in the figure. As will be seen, the electric field is effective to produce killing of biofilm cells at biocide concentrations which are several times lower than normal biofilm biocide concentrations. That is, the electric field shifts the biofilm biocide curve in FIG. 2 toward substantially lower concentrations, i.e., closer to the planktonic biocide curve.

B. Biofilm Potentiation Effect

Figure 3:
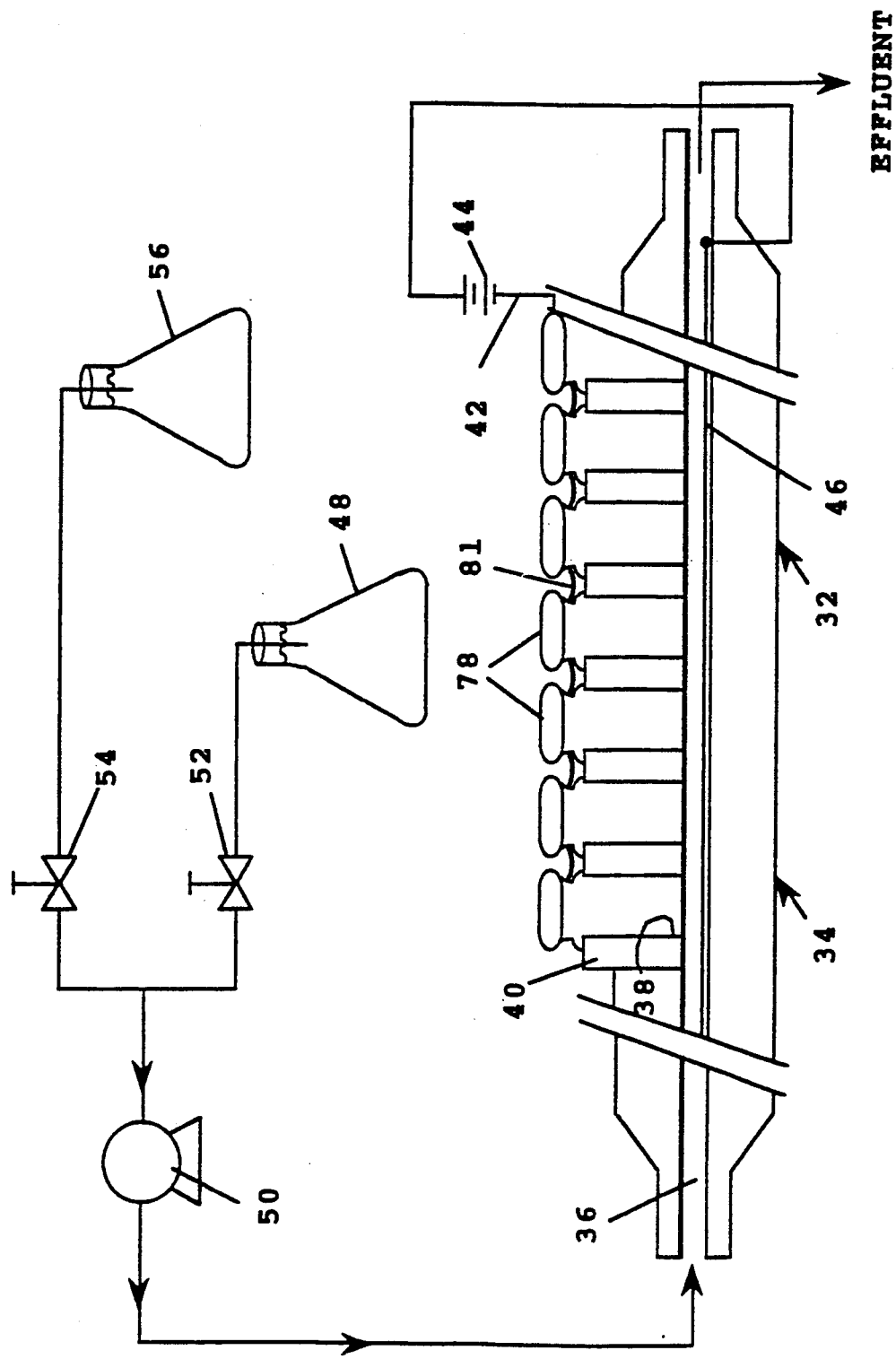
FIG. 3 shows an experimental device used for testing the effect of an electric field on the viability of biofilm cells.

FIG. 3 shows a system for demonstrating the potentiating effects of an electric field on biocide action against biofilm cells. The system includes a Modified Robbins Device (MAD) 32, which includes a flow chamber 34 formed of acrylic block about 40 cm in length, and having an inner channel or lumen 36 with width and height dimensions of 10 mm and 2 mm, respectively. A series of openings, such as openings 38, in the upper side of the block are designed to hold removable conductive blocks, such as blocks 40, with the lower ends of the blocks flush with the upper lumen wall, as shown. The blocks are connected in parallel by a wire 42 to one side of a voltage source 44. A platinum wire 46 extending along the floor of the lumen in the device is connected to the oppositepolarity side of the voltage source.

In operation, a cell suspension is passed through the lumen from a cell-culture reservoir 48 connected to the flow chamber via a pump 50, controlled by a valve 52, until a desired buildup of biofilm on the lower faces of the conductive blocks is achieved. The microorganisms in culture are pumped at a relatively slow rate from the vessel through the MAD. An appropriate flow rate, which allows for sedimentation and deposition of microorganisms as well as delivery of a large number of organisms to the MAD in a period of several hours, is about 60 ml/hour. Typically, biofilms developed under these conditions are expected to have densities of from $1 \times 10^5$ to over $1 \times 10^7$ cells/cm$^2$.

Thereafter, valve 52 is closed and a second valve 54 connecting the pump to a second reservoir 56 is opened, to pass antibiotic treatment solution through the device. At the same time, a voltage is applied across the device, to generate an electric field across the lumen in the device. After a selected treatment time, the blocks in the MAD are removed aseptically and analyzed for viable cell numbers.

Figure 4:
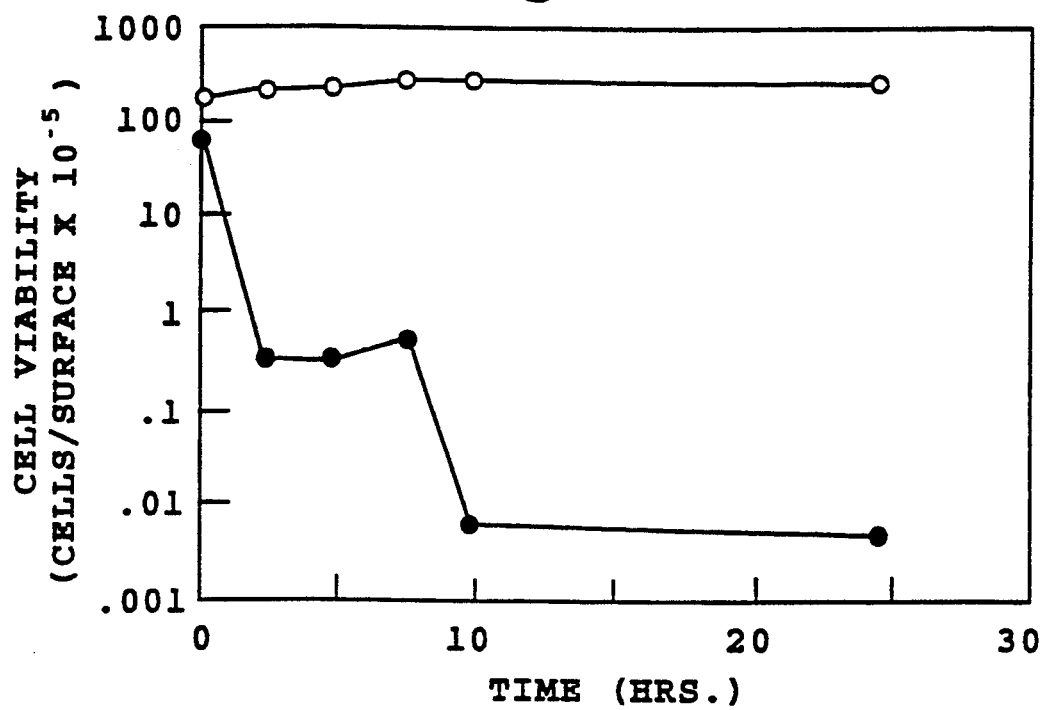
FIGS. 4 and 5 are plots of biofilm cell densities after treatment of P. aeruginosa biofilms with tobramycin (4) or Kathon ® (5) in the presence (solid circles) or absence (open circles) of electric field, as a function of treatment time.

FIG. 4 shows a plot of *P. aeruginosa* cell viability in a biofilm after treatment with the antibiotic tobramycin in the presence (solid circles) and absence (open circles) of an applied electric field, as detailed in Example 1. The concentration of tobramycin was between about 5–10 times the PBC. The biofilm cell density values were calculated as the average of two experiments, except for the 2 and 4 hour time points, where only one value for the electric-field treatment regimen was available. As seen, the number of cells in the biofilm is substantially unaffected by antibiotic alone, but decreases several orders of magnitude over an eight hour period in the presence of an electric field.

Figure 5:
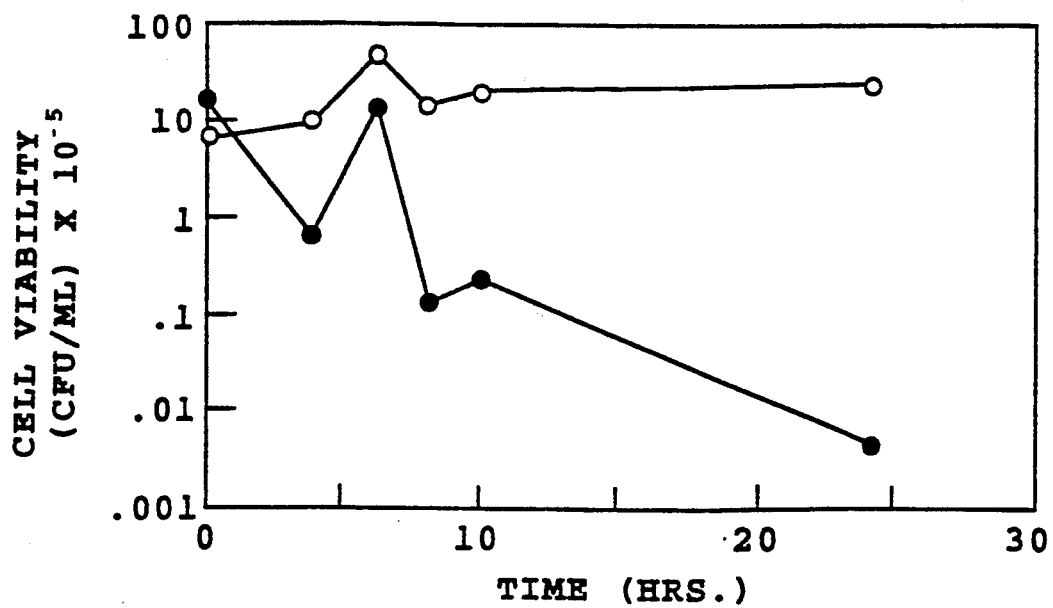

FIG. 5 shows the results of experiments in which *P. aeruginosa* biofilms were treated with the biocide Kathon® at a concentration containing 5 μg/L of the active ingredient isothiazoline, in the presence (solid circles) and absence (open circles) of electric field. As seen, treatment with Kathon® alone did not reduce viable biofilm-associated cell number, whereas treatment with electric field in the presence of Kathon® killed more than 99% of biofilm-associated cells of *P. aeruginosa*. By contrast, Kathon® alone at similar concentrations is effective to eradicate planktonic bacterial cells of *P. aeruginosa*. Table 1 summarizes results from experiments in which 3 different concentrations of Kathon® were tested for effects on planktonic *P. aeruginosa*.

TABLE 1

| Effects of Kathon ® on planktonic *P. aeruginosa* ||
| Concentration | Percent killed |
| --- | --- |
| 2.5 μg/ml | >97 |
| 5 μg/ml | 99.5 |
| 10 μg/ml | >99.7 |

The efficacy of the treatment method in reducing a yeast biofilm fungal infection was examined similarly, by assaying viability of yeast biofilm cells exposed to the antifungal agent cycloheximide, in the presence or absence of electric field. Details of the method are given in Example 2. The change in yeast biofilm cell density, as a function of treatment time in the presence of biocide alone (open circles) or biocide plus electric field (closed circles), is given in FIG. 6, for a 29 hour treatment period. As seen, little or no long-term change in biofilm viability occurred in the absence of electric field, whereas the density of viable cells decreased over 25 fold in the presence electric field.

C. Biofilm Reduction Method

The studies described above are illustrative of the general method of the invention, demonstrating the effectiveness of biocides, in combination with electric field, in reducing biofilm cell viability at biocide concentrations which themselves are relatively ineffective in killing biofilm microorganisms. The results show that bacterial and yeast cell biofilms can be treated effectively, and that a variety of biocide compounds, including compounds from different families of antibiotics, and antifungal agents, are useful in the treatment method.

The biocide used in the method is one which is selected, according to known pharmaceutical principles, for effective killing of the infecting microorganism. For example, an appropriate antibiotic may be selected by testing a culture of the bacterial cells against a panel of antibiotics. Among the antibiotics which are useful in the present invention are those in the penicillin, cephalosporin, aminoglycoside, tetracycline, sulfonamide, and quinolone antibiotic families. Preferred antibiotics also include imipenem, aztreonam, chloramphenicol, erythromycin, clindamycin, spectinomycin, vancomycin, and bacitracin. Among the preferred anti-fungal agents are the imidazole compounds, such as ketoconazole, and the polyene microlide antibiotic compounds, such as amphotericin B.

The desired biocide concentration in the method of the invention is one which is effective in killing the microorganism in planktonic form, but which, by itself, is relatively ineffective in killing biofilm microorganisms. Where the method of the invention is used to killing bio films in vitro, by placing a surface containing the biofilm in an electric field, as illustrated in the configuration in FIG. 3, the biocide is added at an appropriate concentration below the BBC to the aqueous medium in contact with the biofilm, along with electrolyte(s) which serve as current carriers.

Where the method is used in the treatment of a biofilm in vivo, the biocide is administered at doses, and dosing intervals sufficient to produce planktonic biocide doses in the region of the biofilm. Typically, an antibiotic is administered at regular intervals over a 3-7 day period to achieve substantially complete bacterial cell killing. The biocide which is administered typically reaches the biofilm site via the bloodstream or lymphatic system, and thus contacts the biofilm via the body fluid which bathes the biofilm. After the biocide is administered, and reaches a threshold level at the biofilm site, the effect of the biocide in biofilm killing is potentiated by applying an electric field across the biofilm in vivo.

The electric field is applied by a voltage source, which may include a direct current (DC) source, such as a battery, or a conventional alternating current (AC) or pulsed voltage source. The voltage level is typically set to between 0.5-20 volts, preferably between 1-10 volts, and preferably under conditions effective to generate a current of about 5 mamp or greater between the electrodes forming the electric field. The effectiveness of the electric field on biofilm destruction will depend on the strength of the electric field, which in turn depends on the voltage and distance between electrodes, the duration of the field, the concentration of biocide at the biofilm during application of the electric field, and fluctuations in the field.

The electric field is applied until a desired reduction in biofilm is achieved, as determined for example by testing cell viability on a biofilm surface. For in vivo treatment of biofilm infection, the treatment method may be monitored, for example, by assaying for infecting microorganisms systemically or near the site of biofilm infection.

D. Electric Field Effects on Cells

Figure 7:
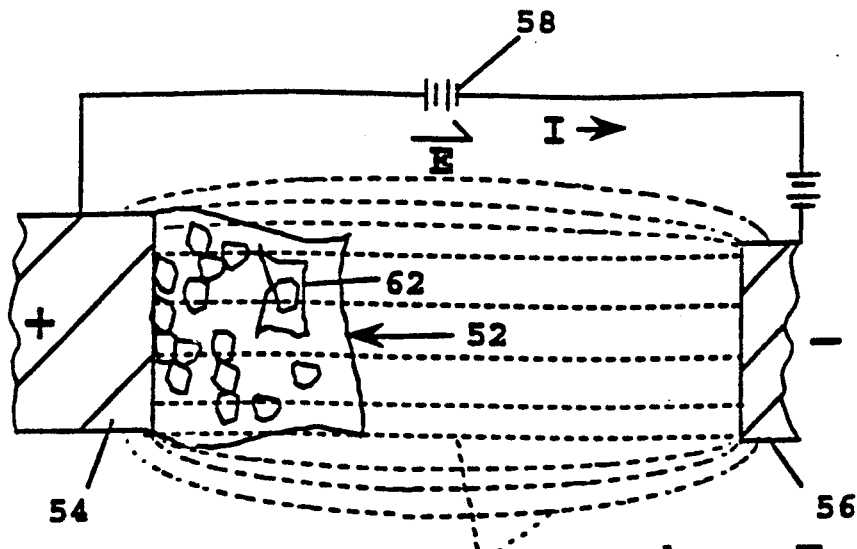
FIG. 7 illustrates the electric field lines in the biofilm configuration shown in FIG. 1.

FIG. 7 shows a configuration in which a biofilm 52 is placed in the electric field E generated between a pair of electrodes 54, 56 which are connected to a voltage source 58 as shown. The electric field lines between the two electrodes are shown by dashed lines, such as lines 60. As seen, the field is strongest in the region directly between the two electrodes, indicated by straight dashed lines, and decreases slightly moving away from this region, according to well-known electric field effects. The flux of ionic species in the aqueous medium between the two electrodes (including the biofilm) follows the electric field effects, and is thus highest in the region immediately between the electrodes and decreases slightly moving away this region. The field lines thus indicate the electric field strength and ion flux that can be expected anywhere in the region between the two electrodes.

Total current flow in the system is due to total ionic species migration in the system, and is thus dependent on the electrolyte concentration in the medium, the distance and size of the electrodes, and the voltage impressed on the electrodes. As noted above, the configuration of the system is preferably such as to produce a current flow of at least about 5 mamp.

Figure 8A:
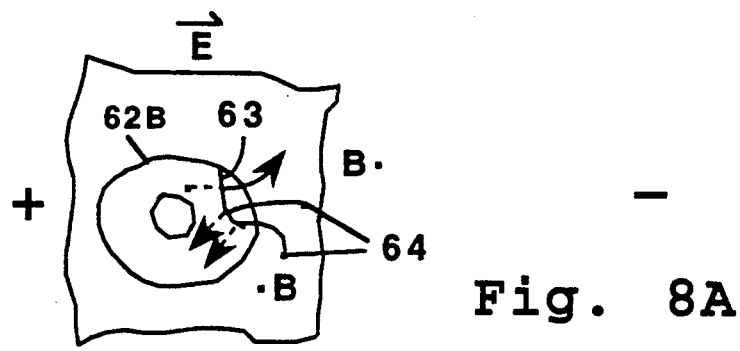
FIGS. 8A–8C illustrate, for a biofilm cell in an electric field, possible mechanisms of biocide potentiating based on (8A) depolarization of transmembrane ion potentials; (8B) mass-ion flow effects; and (8C) membrane disruption.
Figure 8B:
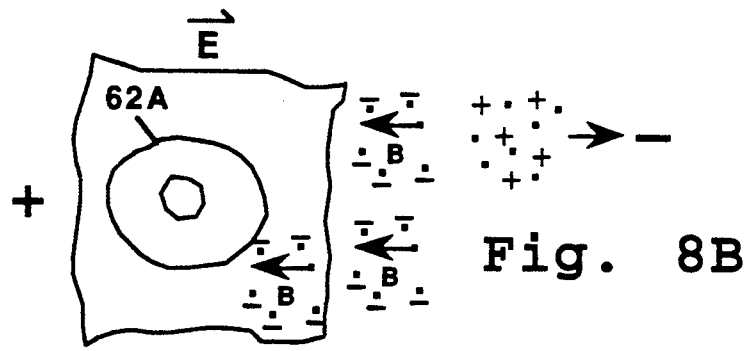
Figure 8C:
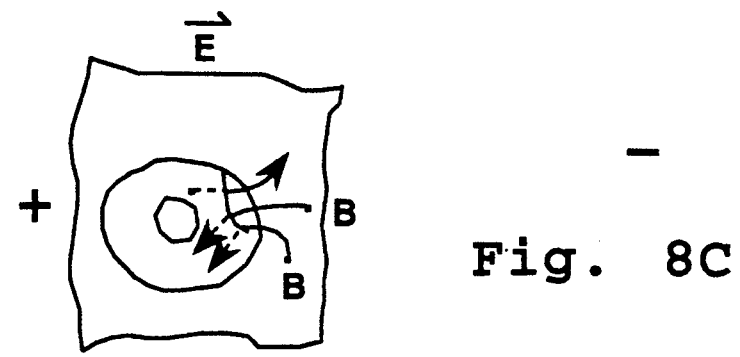

FIGS. 8A and 8B show schematically two possible mechanisms of electric field potentiation of a biocide effect against cells forming a biofilm. The figures each show a cell such as cell 62 in FIG. 7 in an electric field, such as the one generated by electrodes 54, 56 in FIG. 7. FIG. 8A illustrates a biocide-charge effect which acts to increase biocide penetration of the biofilm matrix. The biocide shown in the figure is not charged, but is weakly associated with a number of charge carriers, imparting a net charge (in the illustration, a net negative charge) which causes the biocide to behave as a charged carrier in the electric field. As such, the biocide is drawn electrophoretically into and through the biofilm, essentially reducing the biofilm's ability to exclude biocide molecules. Alternatively, or in addition, biocide migration through the biofilm may be enhanced by increased field-directed disruption of the biofilm matrix.

A second mechanism, shown in FIG. 8B, depends on the ability of the electric field to induce perturbations in the immobilized biofilm cells, such as cell 62B. Such rupture can both increase leakage of intracellular components from the cell, and promote influx of biocide molecules, such as molecules 64, as indicated.

Studies carried out in support of the invention have examined the role which cell membrane perturbation in an electric field may play in the biocide potentiation effect of the present invention. These studies, which employ the MAD system described above, are detailed in Example 3. Briefly, after biofilm formation of $1 \times 10^6 - 1 \times 10^7$ cells on the blocks in the MAD device, an electric field (5 volt, 5-30 mamp) was applied for periods of up to 2 hours. At half-hour intervals, fluid circulating in the MAD was removed, centrifuged to remove planktonic cells, and assayed spectrophotometrically, at 260 nm (nucleic acid absorption peak), 280 nm (protein absorption peak), and 340 nm (NAD/NADH) absorption peak. The results, expressed as an absorption ratio for cells exposed to electric field/non-exposed cells, is given in Table 2.

TABLE 2

| Hours | DNA (260 nm) | PROTEIN (280 nm) | NAD (340 nm) |
|---|---|---|---|
| 0.5 | 1.27 | 1.39 | 1.36 |
| 1.0 | 1.26 | 1.38 | 1.25 |
| 1.5 | 1.17 | 1.28 | 1.14 |
| 2.0 | 1.15 | 1.16 | 1.08 |

The results indicate slightly greater loss of DNA, protein, and NAD/NADH from cells which have been exposed to electric field than non-exposed cells, with the greatest difference in leakage rates occurring within the first hour of exposure to the electric field.

The results suggest that loss of membrane integrity may play a some role in the biofilm potentiation effect, but that the dominant effect is likely to involve increased penetration of the biocide through the biofilm matrix, either because of charged-biocide migration effects or field-directed disruption of the biofilm matrix.

The illustration in FIG. 7, which shows electric field strength as a function of position in an electric field, indicates how these biocide potentiation mechanisms would be expected to vary as a function biofilm position between the two electrodes.

E. Applications

In one general embodiment, the method of the invention is used for reducing biofilms in vitro, by placing a biofilm containing surface in an electric field in the presence of biocide. This application is demonstrated generally by the system shown in FIG. 2, where a biofilm is placed between two electrodes 26, 28 in the presence of a biocide in an aqueous medium which is in contact with the biofilm. As demonstrated in this system, the electric field potentiates the biocide several orders or magnitude, as judged by the loss of biofilm cell viability at biocide concentrations which are normally ineffective in killing biofilm cells.

In a second general embodiment, the method is used for treating biofilm infection in the body, by applying an electric field across an internal biofilm surface. The method of the invention is applicable to disease conditions which involves biofilm growth on a natural tissue surface or bio-implant surface. In the case of biofilm growth on a surface of a bio-implant device, the device itself is preferably provided with at least one electrode and structure for accessing the electrode, for applying a non-ground voltage to the electrode. This is illustrated in the following example for treatment of urinary tract infection (UTI).

The most common predisposing factor for fatal gram-negative sepses that originate in hospitals is UTI (Nichel et al 1985). Although most infections are polymicrobal, gram-negative bacteria, such as *Proteus mirabilis* and *E. coli* account for a large proportion all UTI. The leading cause of such UTI in hospitals is urinary catheters (Warren). Since in-dwelling catheters provide a foreign surface for biofilm formation, effective UTI treatment requires reduction in the biofilm reservoir, as well as treatment of the systemic infection.

Figure 9:
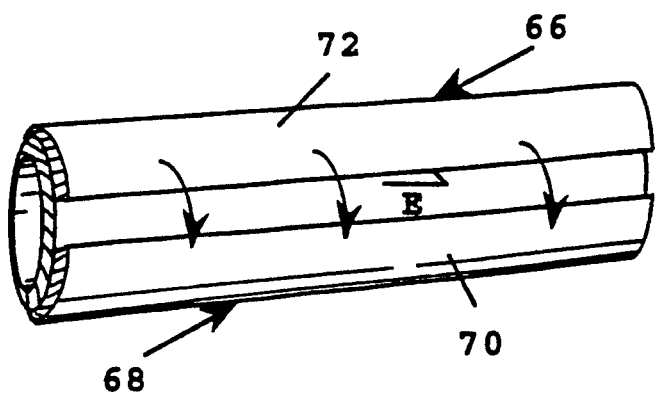
FIG. 9 illustrates a treatment method for urinary tract infection, in accordance with one embodiment of the invention.

FIG. 9 shows a portion of a urinary catheter 60 used in the treatment method. The catheter includes a drainage tube 64 which functions conventionally, and a pair of electrodes 66, 68 extending along the opposite sides of the tube. These two electrodes, which are preferably formed of platinum or other bio-inert conductive material, are connectable at the catheter's proximal end to a voltage source 70 for applying a selected voltage across opposite sides of the catheter. As will be appreciated, the charged electrodes produced a substantially circumferential electric field about the tube, as indicated at E, for killing a biofilm which collects on the catheter surface.

The biocide used in the treatment method is preferably an orally administered antibiotic which appears in the urine, at a PBC concentration or higher, within 1 to 4 hours after administration. Preferred antibiotics which are useful against gram-negative bacteria include broad-spectrum penicillins, such as ticarcillin, sulfonamides, and cephalosporins. These drugs may be used in combination with each other, with other antibiotics such as parenterally-administered aminoglycosides, or in combination with other drug-enhancing agents such as penicillinase inhibitors (clavulanate, sulbactam) or as in the combination of sulfamethoxazole with imethoprim.

After drug administration, a preferably 1-5 volt potential is applied across the two electrodes, and the resulting electric field is applied for typically 1-4 hours during maximum concentration of antibiotic agent in the urine. The treatment may be repeated at periodic intervals, e.g., once a day during the period of catheter use, to insure that biofilm growth is suppressed during the period of catheter use.

The treatment method just described is applicable to other medical procedures in which catheter, vascular access ports, and other temporary in-dwelling appliances are used. For example, in peritoneal dialysis by an in-dwelling catheter, where biofilm formation is known to be a source of continued infection (Read), the biofilm may be treated by administering an antibiotic for delivery into the peritoneal cavity, and generating an electric field across spaced regions of catheter, in a radial direction, using the catheter as a single electrode.

Similarly, bacterial colonization of a Hemasite access device (Reed) can be controlled, particularly in the transcutaneous regions, by combining electric field generation with antibiotic administration, such as topically in the transcutaneous zones.

Prostate infection commonly occurs spontaneously or as a complication of chronic catheterization in elderly males. Under usual treatment methods, the patient is given a antibiotic treatment which may involve oral doses of ampicillin or one of the cephalosporins over a 7- to 10-day dosing period. This treatment is generally effective to eliminate symptoms of localized infection. However, infection may recur within a several-month period, evidencing latent infection, presumably in a biofilm reservoir, which was not destroyed by the antibiotic treatment.

In the present treatment method, antibiotic administration is accompanied by electric field generation by the indwelling catheter, as described above. In the treatment method, an antibiotic, such as ticarcillin, cefaclor or gentramycin is administered orally, intramuscularly, or intravenously to the patient. When the antibiotic has reached a desired level in the region of infection, a voltage, preferably 1-5 volts, is applied to the catheter to produce the desired electric field in the region of the biofilm. The electric field is applied typically for 1-4 hours during maximum concentration of antibiotic agent in the infected region. The treatment may be repeated at periodic intervals, e.g., once a day over a two-week period, to insure that biofilm growth is eliminated.

In another aspect, the invention includes a body implantable device designed for use in biofilm reduction, in accordance with the treatment method disclosed above. The device has one or more surfaces, or surface expanses which are exposed to body fluids, and on which biofilm formation can occur. Electrode structure in the device is designed for generating an electric field across the surface expanse(s), for biofilm reduction in the presence of biocides. Preferably, the electrode structure allows the generation of an electric field whose field strength is sufficient to produce increased leakage of cellular contents from microorganisms which form the biofilm.

The use of the method, for treating biofilm in vivo, is illustrated by the following example, which is illustrated in FIGS. 10A and 10B, and FIG. 11. The first of these figures show, in side and top views, respectively, a flow cell 80 having a boat-shaped chamber 82 through which fluid can be circulated, via inlet and outlet conduits 84, 86, respectively. Within the chamber is an electrode plate 88 which includes fives stainless steel bars which are indicated E1, I1, E2, I2, and E3 in FIG. 10B. Bars E1 and E3 are electrically connected to constitute one electrode of a direct-current voltage source (not shown). Bar E2 is connected to constitute the other electrode of the voltage source. I1 and I2 are not directly connected to the driving voltage.

In operation, planktonic bacteria, in this example, *Pseudomonas aeroginosa*, are flowed through the flow chamber so that extensive bacterial biofilms form on all available surfaces including those of the steel bars. To achieve biofilm reduction on the bars, a 2 volt driving voltage was applied between the two electrodes, one double and one single, generating a field strength of about 1.5 V/cm, and a minimum current density of about 15 $\mu A/cm^2$. The polarity of the electrodes was switch every 64 sec. When this driving voltage was applied in the presence of 2× the concentration of tobramycin necessary to kill planktonic cells (in this example, Pseudomonas aeroginosa), which is 1/250× the concentration usually needed to kill biofilm cells, all biofilm cells on all 5 elements are killed in just over 24 hours (a very few left at 24 hours, none at 48 hours). The antibiotic was carried in a physiological salt solution and flowed through the cell at a rate of about 1 ml/min. No significant killing of biofilm bacteria is seen when either the electric field or the antibiotic are used alone.

Scanning electron microscopy (SEM) of the 5 element test device shows that the "high-field" edges of the electrodes (insides of E1 and E3, both sides of E2) have no biofilm left and the individual cells that remain are broken and disrupted. The "low-field" surfaces of the electrodes (outsides of E1 and E3, middle of E1, E2, and E3, and all of I1 and I2) had no living biofilm cells but the biofilms were intact with undisturbed cells in slime and still adherent to the surfaces.

To demonstrate in vivo biofilm reduction, the 5-element electrode plate from above was enclosed in the flow cell, and the inside of the flow cell was colonized with biofilms by flowing bacteria through it for 24 hours. The colonized electrode plate was then implanted in the peritoneum of a rabbit, as shown in FIG. 11. Tobramycin at 2 MIC was infused into the area through a tube 90, so that body fluids and antibiotic would be passing through the test device, past the 5 steel bars, and the excess fluid was drained through a tube 92, as indicated. The electrode leads for bars E1 and E3, and for bar E2 were attached to opposite electrodes, as above, and a driving voltage of 2 volts DC, with alteration of polarity every 64 seconds, was applied. The rabbit appeared undisturbed, and ate normally during the 24 hour treatment period.

Analysis of all 3 electrode bars slabs showed no living biofilm bacteria after the treatment period. I1 was also entirely sterile and I2 showed very small numbers ($1 \times 10^2$) of surviving biofilm bacteria. The example shows that biofilm bacteria can be killed by the treatment method of the invention without damage or discomfort to the animal. By contrast, when an animal was treated with antibiotics alone, but no applied voltage, the animal died of bacterial infection.

From the foregoing, it can be appreciated how various objects and features of the present invention are met. The treatment method allows biofilm infections, which are often difficult or impossible to treat by biocide treatment alone, to be effectively controlled or eliminated at tolerated biocide levels, by potentiating the biocide effect selectively in the region of biofilm growth.

The electric field used for potentiating biocide effect is itself safe and generally easy to generate, either by direct connection to a voltage source, or by magnetic induction. The examples reported above show that a current density as low as 5–25 $\mu A/cm^2$ is effective in the method. The method is applicable to a wide range of biofilm infections involving both natural tissue surface or bio-implant surfaces.

The following examples illustrate specific treatment methods which demonstrate the application of the method to various bacterial and yeast organisms. The examples are intended to illustrate, but not limit, the scope of the invention.

EXAMPLE 1

Treatment of P. aeruginosa biofilms

A. Experimental biofilm formation

A Modified Robbins Device (MAD) described in FIG. 4 was sterilized (ethylene oxide) prior to connection of the platinum wire leads to the poles of a constant output 20 volt power source. The power source was calibrated to deliver a 20 or 40 milliamp current. The polarity of the current was alternated every 4 seconds.

Biofilms were formed on the inner surfaces of the lumen of the MAD by connecting the MAD by tubing to a 1.6 liter vessel containing an 8 hour exponential phase culture of Pseudomonas aeruginosa. Planktonic cells in 20:80 Mueller Hinton Broth (M56, supplemented with 1% glucose) from cultures of Pseudomonas aeruginosa were allowed to flow through control (uncharged) and experimental (charged) MAD's at a rate of 60 ml/hr for several hours, in the absence of electrical current, until substantial biofilms of adherent bacteria had formed on all the internal surfaces of the MAD's, including the steel sampling studs. Typically the biofilms of P. aeruginosa developed to a level greater than $1 \times 10^7$ cells/cm$^2$, as determined by plating of detached and separated biofilm bacteria.

Prior to experimental manipulations, 100 ml sterile double distilled water was run through the devices in order to remove planktonic phase cells. During treatment, an electrolyte solution containing tobramycin (5 mg/l) was aseptically supplied to the device from a second reservoir.

Sessile bacteria were counted by plating techniques (BHI agar, half strength) following their removal from the sampling studs by vigorous scraping, vortex mixing, and low energy ultra-sonication (Nickel et al., 1985a). Sessile bacteria were additionally directly visualized by examination of the colonized sampling studs by scanning electron microscopy (SEM) after preparation by critical point drying and metal evaporation.

B. Treatment with tobramycin

Comparison of treatment of P. aeruginosa with antibiotic (tobramycin, 5 mg/l) alone and with tobramycin (5 mg/l) in the presence of electric field (5 V, 10–15 mA) was carried out in duplicate for samples treated with either antibiotic alone, or antibiotic plus electric field. Sampling studs were removed at intervals to assess the degree to which sessile bacteria were killed by treatment. The concentration of antibiotic used to treat the biofilms was selected to fall between the Planktonic Biocidal Concentration (PBC) needed to kill planktonic cells and the Biofilm Biocidal Concentration (BBC) usually needed to kill adherent bacterial Within biofilms on colonized surfaces (Nickel et al., 1985a). The results are shown in FIG. 5A and discussed above.

C. Treatment with Kathon ®

Conductive and non-conductive MAD's were colonized with P. aeruginosa as described in Example 1.A. above. Following a brief (100 ml) wash with 100 ml distilled water, the MAD's were connected to reservoirs containing Kathon ® (isothiazoline) at a concentration of 9 $\mu$g/L active ingredient. Conductive MAD's were then subjected to DC electric field (5 V, 10–15 mA) for a period of up to 24 hours. Sampling blocks were removed at the time intervals shown in FIG. 7B, which plots cell biofilm cell density, expressed as colony forming units (CFU)/ml taken from the electrodes, as a function of treatment time. Cell densities measured after biocide treatment in the presence and absence of electric field are indicated by solid and open circles, respectively in FIG. 7B, discussed above.

EXAMPLE 2

Treatment of *Candida albicans*

Conductive and non-conductive MAD's were colonized for 24 hours with *C. albicans* by exposure to planktonic culture under the conditions described in Example 1A, above. Planktonic culture concentrations ranged from less than $3 \times 10^5$ to approximately $1 \times 10^8$ during the 24 hour biofilm formation period.

Figure 6:
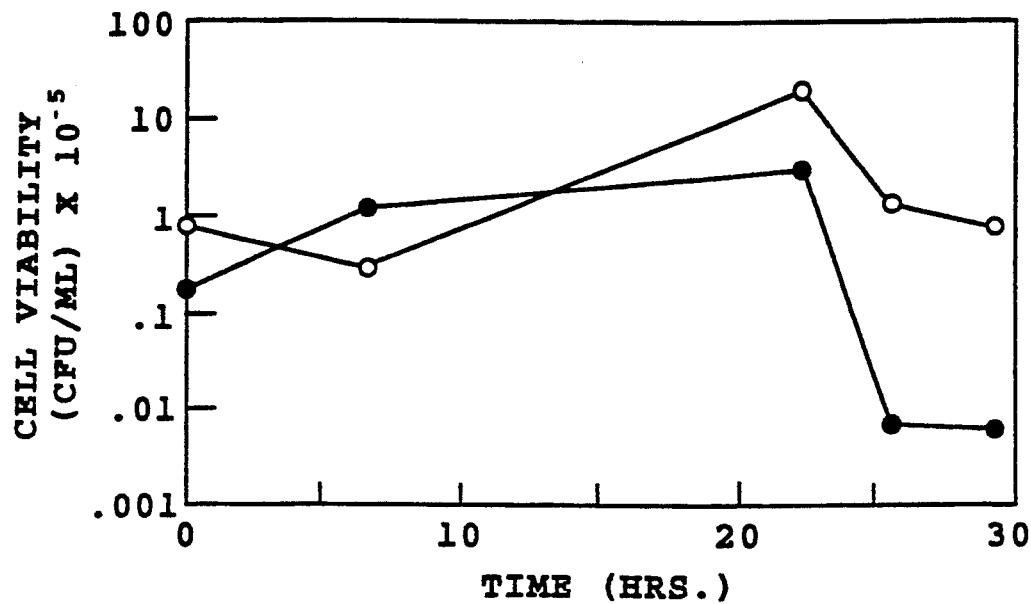
FIG. 6 is a plot of biofilm cell densities after treatment of C. albicans biofilms with cycloheximide in the presence (solid circles) or absence (open circles) of electric field, as a function of treatment time.

In the treatment method, *C. albicans* biofilms were treated with 100 ppm cycloheximide in the presence of absence of an electric field (5 V, 10-15 mamps). After the treatment times indicated in FIG. 6, cells were removed from the colonized electrodes, and cell density, expressed in CFU/ml, was determined as above. The results are shown in FIG. 6, discussed above.

EXAMPLE 3

Effect of electric current on bacterial cell integrity

Biofilms of *P. aeruginosa* or *S. aureus* cells were grown on electrodes of an MAD as described in Example 1. Biofilm formation occurred over an 8 hour period during flow of cells through the device. After colonization, a 5-volt potential was applied across the electrodes in one of the MRDs, with change in polarity every 64 seconds. Current at this voltage level was between 5-30 mamp.

After 0, 0.5, 1, 1.5, and 2 hours of electric field application, an aliquot of cell suspension in each MAD (no electric field, and 5-V electric field) was removed, centrifuged to remove cells, and the supernatant was measured for optical absorbance at 260 nm (DNA absorbance peak), 280 nm (protein absorbance peak), and 340 nm (NAD/NADH absorbance peak). The ratio of absorbance readings $OD_+/OD_-$ (electric field/no electric field) at the three absorbance wavelengths is shown in Table 2, discussed above.

Although the invention has been described with reference to particular methods of treatments and implant devices, it will be appreciated that a variety of changes and modifications can be made without departing from the invention.

We claim:

1. A method of killing microorganisms which (a) form a biofilm on a surface expanse, and (b) are refractory to killing when a planktonic biocidal concentration of a biocide effective against the microorganisms in planktonic form is administered, comprising
    contacting the surface expanse with an aqueous medium containing the biocide in such planktonic biocidal concentration, and
    during said contacting, applying a voltage across the biofilm, to generate an electric field whose field strength of at least about 5-25 $\mu A/cm^2$ and duration are sufficient to produce killing of such microorganisms forming the biofilm.

2. The method of claim 1, wherein the biofilm is composed predominantly of bacteria, and said biocide is an antibiotic selected from the family of antibiotics consisting of penicillins, cephalosporins, aminoglycosides, tetracyclines, sulfonamides, macrolide antibiotics and quinolones.

3. The method of claim 1, wherein the biocide is selected from the group consisting of imipenem, aztreonam, chloramphenicol, erythromycin, clindamycin, spectinomycin, vancomycin, rifampin, bacitracin, methenamine, tobramycin, and nitrofurantoin.

4. The method of claim 1, wherein the field strength produced by said generating is effective to produce a substantial leakage of intracellular material from the cells forming the biofilm as evidenced by release of DNA, protein or NAD/NADH from such cells.

5. The method of claim 1, for use in treating a biofilm-related infection in the body, wherein said contacting includes administering a biocide at a dosage effective to produce such planktonic biocidal concentration at the biofilm site during such generating.

6. The method of claim 5, wherein said current density is generated by placing a voltage across a pair of electrodes which are implanted at the biofilm site.

7. The method of claim 5, for use in treating infections in or adjacent an identified region of a vessel which is accessible by a catheter extending from an external body site to such vessel region, wherein said generating includes placing into said vessel region, a catheter having an electrode which extends along at least a portion of said vessel region, when the catheter is so placed, and applying a voltage to the catheter electrode.

8. The method of claim 7, wherein said biofilm is associated with a prostatitis infection, and said vessel region is the region along the urethra which passes through the prostate gland.

9. The method of claim 1, wherein said surface expanse is formed by a biocompatible surface of an implanted device, and said generating includes applying an electric field across such surface.

* * * * *